(12) United States Patent
Cayre

(10) Patent No.: US 8,709,786 B2
(45) Date of Patent: Apr. 29, 2014

(54) DEVICE AND PROCESS FOR ISOLATING AND CULTIVATING LIVE CELLS ON A FILTER OR EXTRACTING THEIR GENETIC MATERIAL

(75) Inventor: Yvon Cayre, Paris (FR)

(73) Assignee: Screencell, Paris (FR)

( * ) Notice: Subject to any disclaimer, the term of this patent is extended or adjusted under 35 U.S.C. 154(b) by 0 days.

(21) Appl. No.: 13/387,039

(22) PCT Filed: Nov. 4, 2010

(86) PCT No.: PCT/FR2010/052380
§ 371 (c)(1),
(2), (4) Date: Jan. 25, 2012

(87) PCT Pub. No.: WO2011/055091
PCT Pub. Date: May 12, 2011

(65) Prior Publication Data
US 2012/0129164 A1 May 24, 2012

(30) Foreign Application Priority Data
Nov. 4, 2009 (FR) ..................................... 09 57805

(51) Int. Cl.
*C12N 1/08* (2006.01)
*C12Q 1/68* (2006.01)
*C12M 1/12* (2006.01)

(52) U.S. Cl.
USPC .......... 435/270; 435/6.1; 435/283.1; 422/527

(58) Field of Classification Search
None
See application file for complete search history.

(56) References Cited

U.S. PATENT DOCUMENTS

| | | | |
|---|---|---|---|
| 3,731,806 A | | 5/1973 | McCormick |
| 5,284,570 A | * | 2/1994 | Savage et al. ................. 600/345 |
| 5,976,824 A | | 11/1999 | Gordon |
| 6,168,718 B1 | * | 1/2001 | Sutter et al. ................... 210/651 |
| 2005/0139547 A1 | * | 6/2005 | Manoussakis et al. ....... 210/645 |
| 2005/0214737 A1 | * | 9/2005 | Dejneka et al. .................... 435/4 |
| 2007/0105156 A1 | | 5/2007 | Togawa et al. |
| 2009/0226957 A1 | | 9/2009 | Paterlini-Brechot |
| 2011/0070642 A1 | | 3/2011 | Cayre |

FOREIGN PATENT DOCUMENTS

| | | |
|---|---|---|
| FR | 2926091 | 7/2009 |
| WO | WO 2006/100366 A2 | 9/2006 |
| WO | WO 2009/106760 A2 | 9/2009 |

* cited by examiner

*Primary Examiner* — Betty Forman
(74) *Attorney, Agent, or Firm* — IM IP Law PLLC; C. Andrew Im

(57) ABSTRACT

The process for isolating live cells on a filter or extracting their genetic material. The process comprises the steps of attaching, at least temporarily, a filter to a lower opening of a compartment having, in addition, an air inlet; inserting into the compartment a liquid carrying the cells; and attaching, in an impermeable manner, a needle, at least temporarily, to the compartment opening, the filter being positioned between the needle and the interior volume of the compartment. The process further comprises the steps of perforation, with the needle, of a plug of a vacuum tube with negative pressure relative to ambient pressure; and aspiration, by means of negative pressure from the vacuum tube, of the liquid through the filter, the filter retaining the cells.

18 Claims, 13 Drawing Sheets

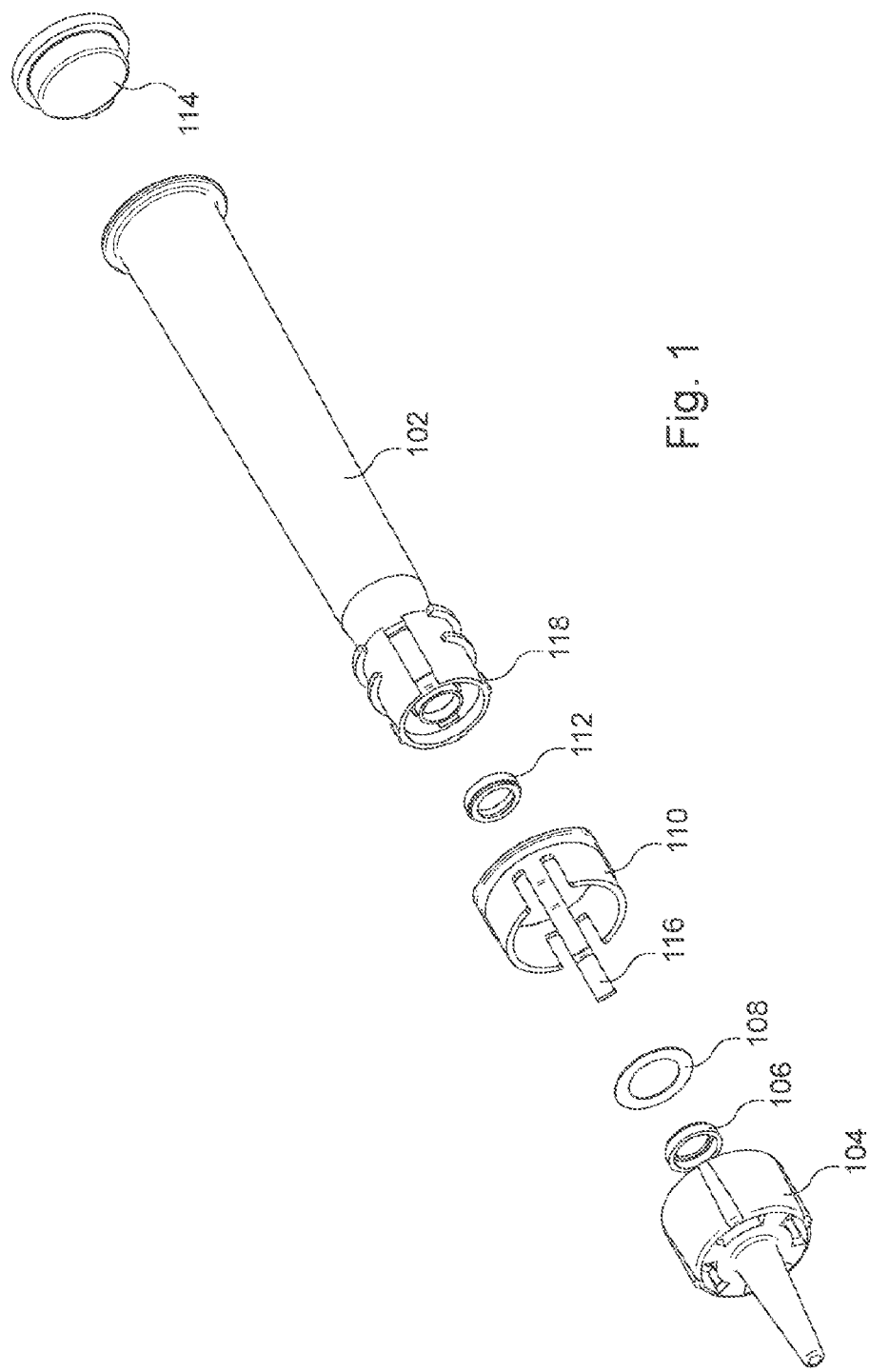

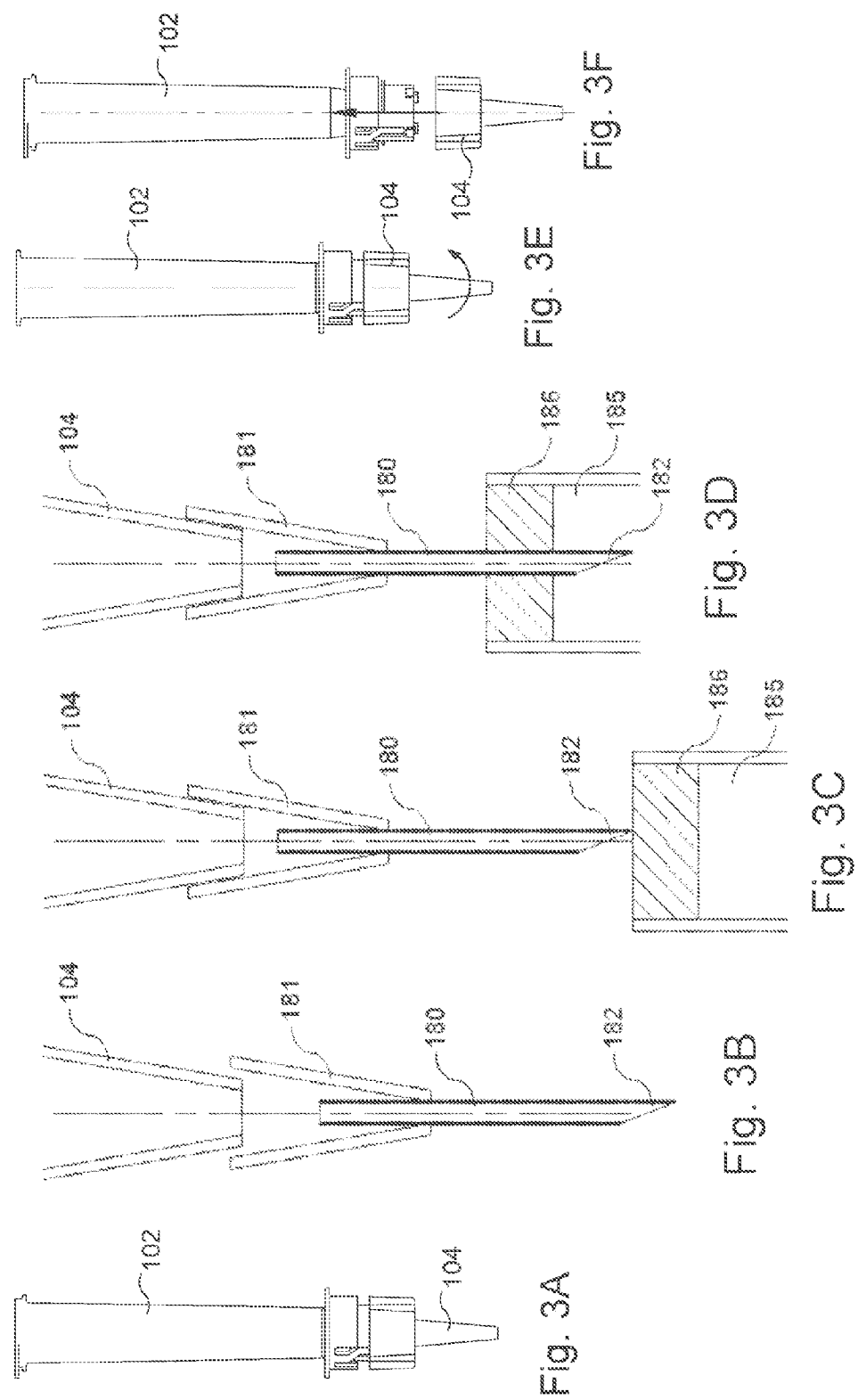

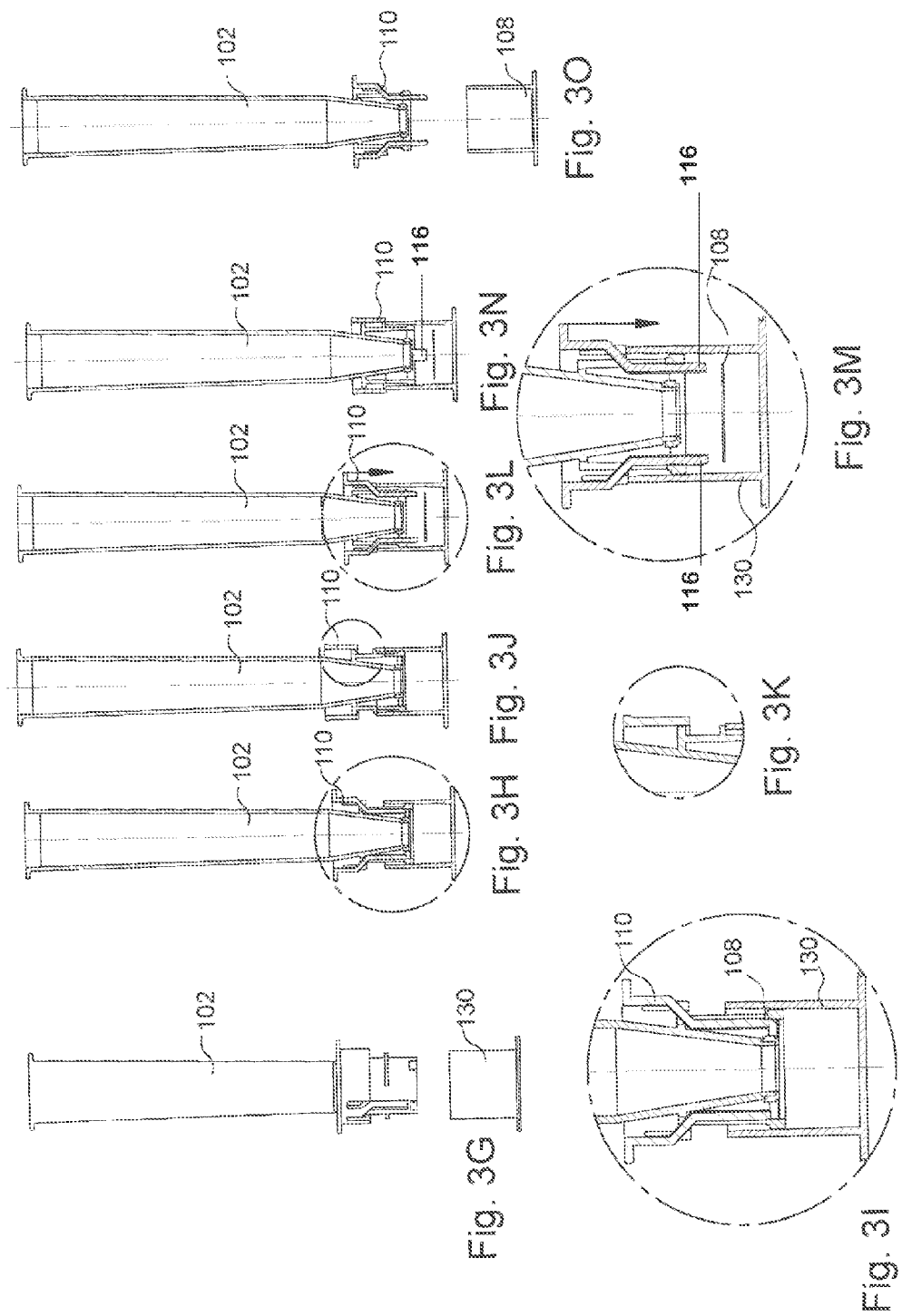

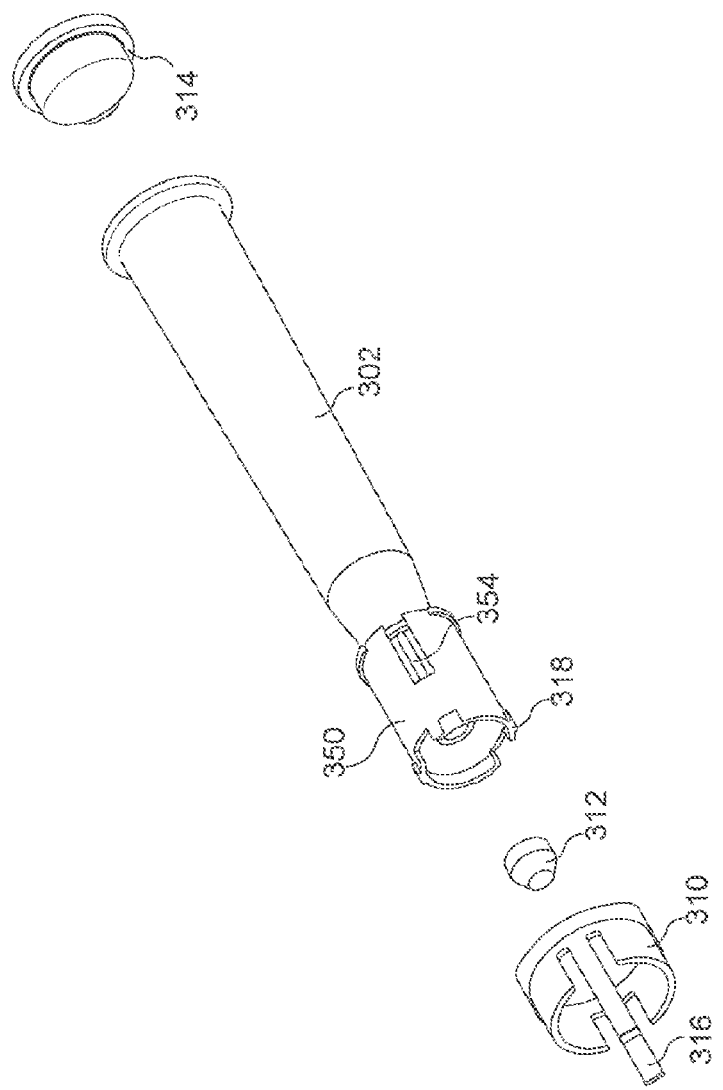
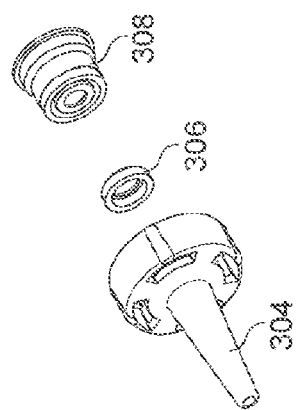

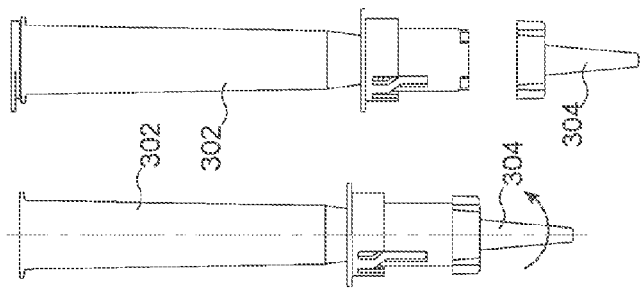
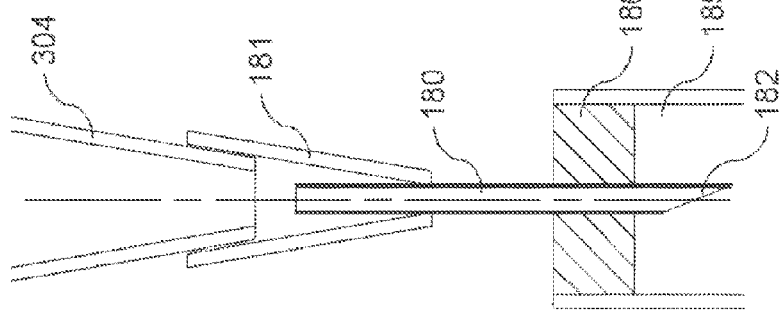
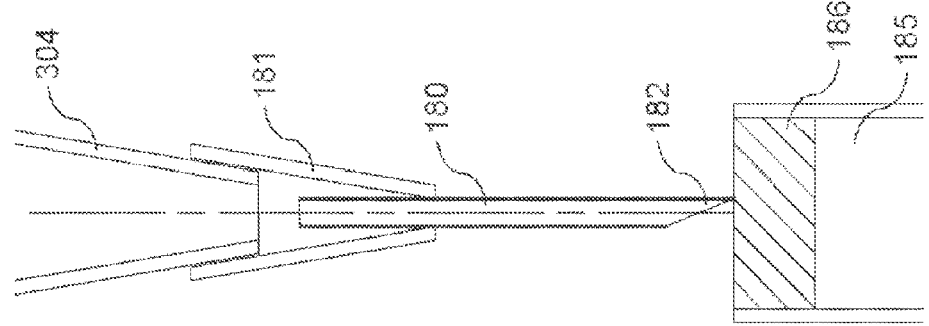
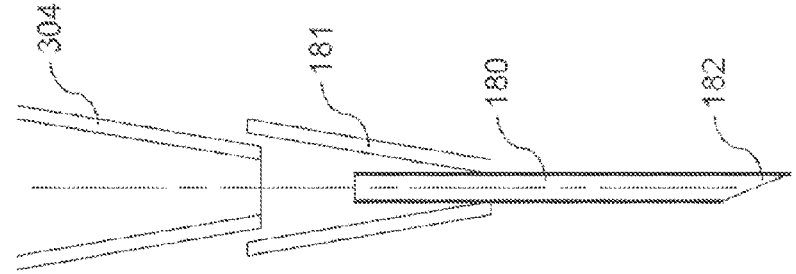
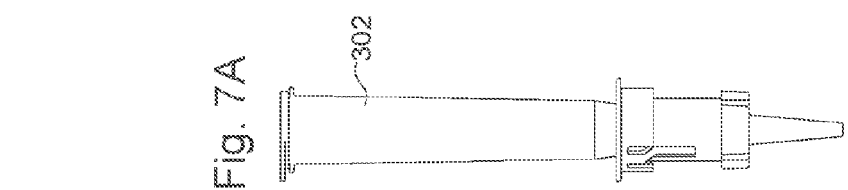

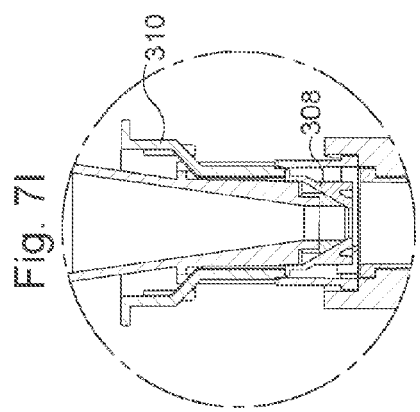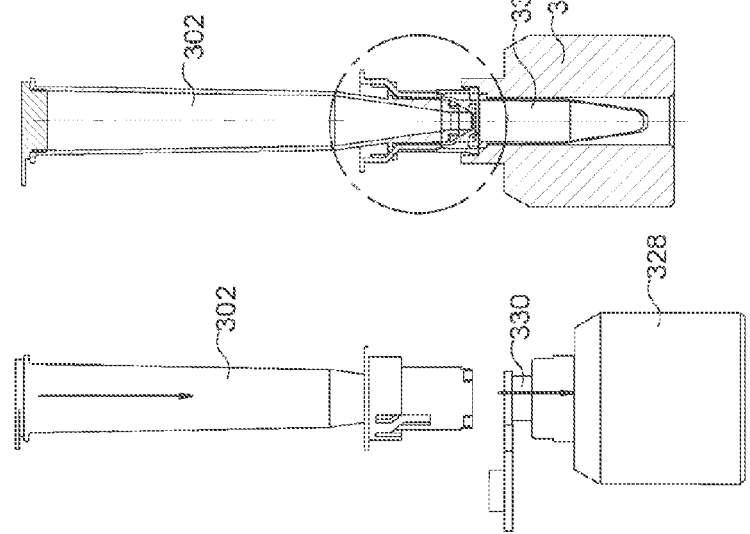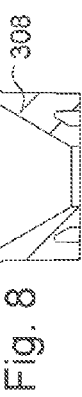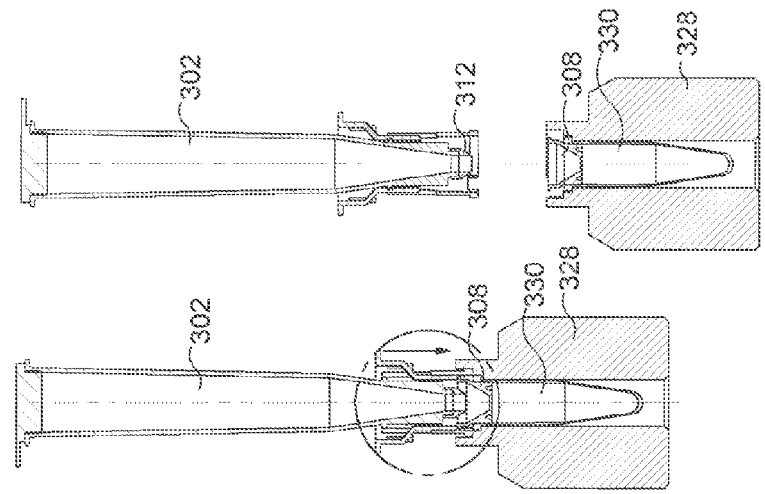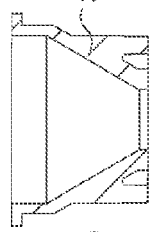

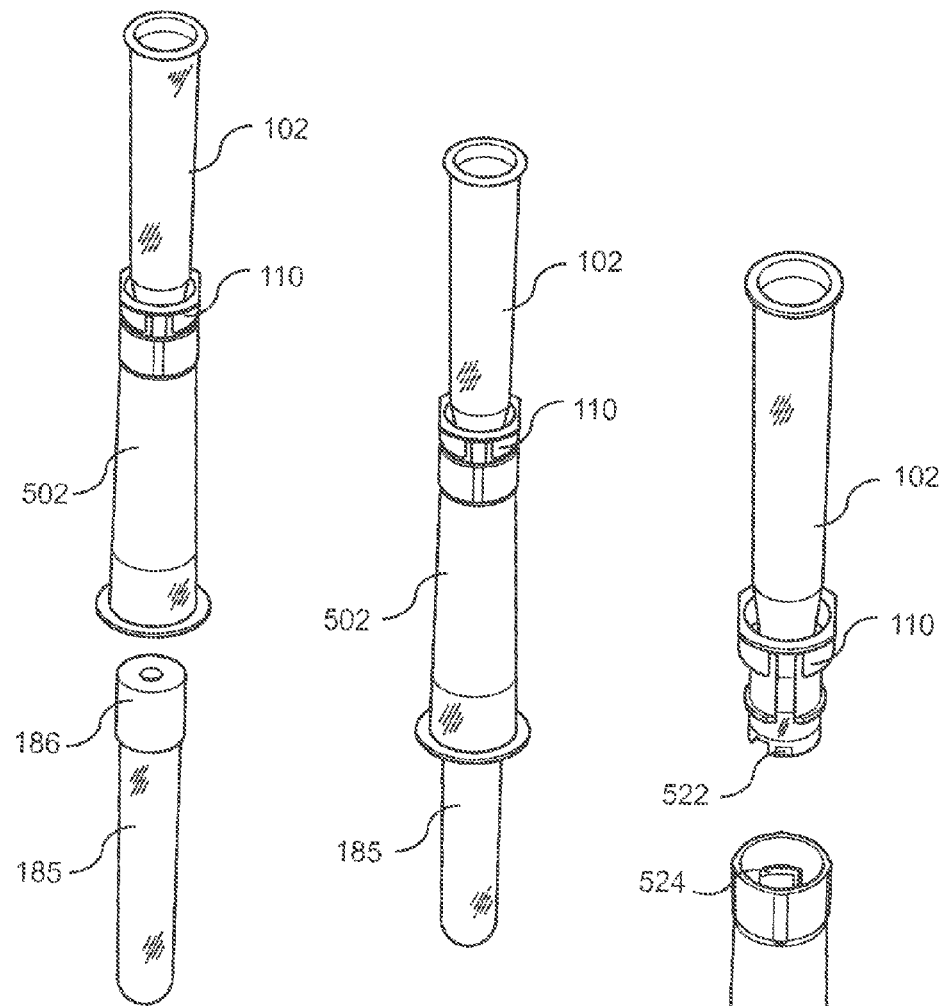

us 8,709,786 B2

DEVICE AND PROCESS FOR ISOLATING AND CULTIVATING LIVE CELLS ON A FILTER OR EXTRACTING THEIR GENETIC MATERIAL

RELATED APPLICATIONS

This application is a §371 application from PCT/FR2010/052380 filed Nov. 4, 2010, which claims priority from French Patent Application No. 09 57805 filed Nov. 4, 2009, each of which is incorporated herein by reference in its entirety.

TECHNICAL FILED OF THE INVENTION

The present invention relates to a device and a process for isolating and/or cultivating live or fixed cells on a filter in order to conduct all cellular analyses (cytology, immunochemistry, FISH trials, etc.) or extract genetic material, amplified if necessary, from live or fixed cells isolated on a filter. It applies in particular to isolating and/or cultivating particular cells present in a liquid, especially blood, or extracting the genetic material of these particular cells.

BACKGROUND OF THE INVENTION

Particular blood cells, for example tumor cells or trophoblasts, are present in very small proportions and must be counted prior to conducting cytological analyses.

It is known that a formaldehyde-based binding buffer is to be applied to a blood sample in order to fix the desired cells, and the resulting liquid then passed through a porous filter. This filter is then used to examine the desired cells on it under a microscope in a laboratory. However, it is not possible to obtain live cells using this procedure.

Such being the case, the inventor has determined that obtaining live cells would make it possible to identify specific markers and, under good conditions, to apply molecular biology, cytogenetic and FISH (the acronym for "Fluorescence In Situ Hybridization") techniques in diagnosing genetic abnormalities in tumor or trophoblastic cells.

The purpose of the present invention is to remedy these disadvantages and to meet this requirement by making it possible, under conditions compatible with standard laboratory testing, to collect live cells which can subsequently be cultivated in appropriate media in the presence of suitable growth factors.

The present invention also relates to the extraction of genetic material amplified if necessary from cells isolated on a filter and the detection of variations and gene expression levels for sensitivity and resistance to target treatments or for genetic abnormalities.

It applies in particular to the collection and potential uniform amplification of the DNA or RNA of particular cells present in a liquid, especially blood.

It is known, for example from the document PCT/FR 2006/000562, that a formaldehyde-based binding buffer is to be applied to a blood sample to fix the desired cells being sought, and the resulting liquid then passed through a porous filter. This filter is then analyzed under a microscope in a laboratory to detect the cells on it. The cells can then be sampled on the filter for analysis, for example by genetic analysis.

However, this procedure cannot be reproduced on a large scale at a reasonable cost, owing to the time, materials and precision of the work involved. Such being the case, reproduction on a large scale and at a reduced cost would enable molecular biology analyses to be conducted both on tumor cells and trophoblastic cells. Furthermore, fixing cells with formaldehyde does not allow good quality genetic material to be obtained: the DNA is partially degraded and forms bridges with ambient proteins and RNA extraction is virtually ruled out.

OBJECT AND SUMMARY OF THE INVENTION

The purpose of the present invention is to remedy these disadvantages and to meet this requirement by making it possible, under conditions compatible with standard laboratory testing, to collect a large proportion of the cellular material, particularly RNA and DNA, in good condition from the cells under consideration. It should also be noted that the present invention makes it possible to isolate fixed cells using a fixative with or without formaldehyde.

For this purpose, the present invention, according to one aspect, relates to a device for isolating fixed or live cells on a filter, characterized in that it includes:

a compartment with an interior volume for receiving liquid carrying said cells, a lower opening and an air inlet, a filter forming a single unit, at least temporarily, with said compartment opening, for retaining said cells when the liquid is passed through the filter, a needle forming a single impermeable unit, at least temporarily, with said compartment opening, the filter being located between the needle and the interior capacity of the compartment, said needle being designed to pierce the plug of a vacuum tube with negative pressure relative to ambient pressure in order to aspirate the liquid through said filter.

Thanks to these features, this device enables the isolation and collection on a filter of the fixed live cells of interest, or of live cells in conditions perfectly compatible with their culturing in order to carry out testing for cytological characterization, and cytogenetic testing, for any other cellular test or to extract genetic material from them.

This collection is carried out directly on the filter with virtually no loss of the desired cells. In this way, a large proportion of the cells under consideration are collected at a reduced cost, in good condition, and under conditions compatible with a routine culture in a laboratory. The isolated cells can be used before or after culturing, for cellular or molecular biology testing.

The device constituting the present invention also enables the collection of cellular material from particular cells in a rapid and efficient manner, for example, after completion of:

a filtration stage during which the major portion of the liquid and said other cells pass through a filter having micropores of an intermediate diameter between that of said particular cells and that of other cells, a lysis stage whether or not followed by DNA and/or RNA amplification in said compartment and a stage for the collection of the genetic material from lysed cells, on the filter.

The device constituting the present invention has numerous advantages:

1) filtration can be performed on a rack or while holding the device in one's hand, resulting in significant savings of time and material (in particular, the use of a vacuum pump and an adaptor box is avoided), 2) filtration can be performed in a sterile hood.

3) filtration can be performed with the device in an oblique position, even virtually horizontal.

4) the conditions are perfectly standardized, the sampling tube being produced in a standardized manner with a pre-defined vacuum capacity.

5) the conditions of use involve enhanced safety conditions, so that it can be operated entirely within a sterile hood;

moreover, once the vacuum tube is filled, it can be removed like a normal blood sampling tube, as the collected blood does not come into contact with the operator.

According to particular features, the device of the present invention as briefly outlined above, additionally comprises a connection means between the compartment and a protective cylinder encircling the needle and designed to encircle the vacuum tube, at least in part, during aspiration of the liquid towards the filter.

Thanks to these provisions, the user is protected against being accidentally pricked with the needle. Furthermore, by using the protective cylinder as a guide, the positioning of the vacuum tube is made easier. The vacuum tube is also kept more firmly in position during aspiration, which prevents it from being removed or displaced so that air enters the vacuum tube by passing next to the needle in the vacuum tube plug. The risk of sample contamination by the user is minimized, as the user cannot inadvertently touch the needle.

According to particular features, the device of the present invention, as briefly described above, comprises, at least provisionally, said protective cylinder.

In this way, the protection of the needle, the sample and the user is assured.

According to particular features, said connection means is provisional and enables the protective cylinder to be removed jointly with the vacuum tube and the needle.

In this way, the protection of the needle and the user is guaranteed after the protective cylinder is separated from the compartment.

According to particular features, said protective cylinder comprises a removable film sealing its opening facing the connection means, the opening through which the vacuum tube is inserted into the protective cylinder.

Thanks to these provisions, the user removes the film before inserting the vacuum tube. This film provides better protection from the user and from the needle as well as a reduction in the risk of sample contamination.

According to particular features, the device of the present invention additionally comprises a removable filter support made of surgical steel designed to be temporarily joined to the lower opening of the compartment.

Thanks to these provisions, the filter can be removed with its holder for cultivating or analyzing the cells collected on the filter or for extracting the genetic material from them. Moreover, the steel is not toxic to the cells collected on the filter.

According to particular features, the thickness of said ring is designed to enable it to be scanned.

According to particular features, said ring carries an identifier.

In this way, this identifier, and thus the collected cells, can be associated with a patient. Errors are thus avoided.

According to particular features, the device of the present invention additionally comprises a mobile means relative to said compartment for applying force to the filter support and releasing said filter support.

As the entire filtration module is sterile and prepared using standards normally applied for molecular biology, any contamination or deterioration of the live cells on the filter or of the genetic material can be avoided. The contents of the compartment are preserved in a sterile state while being handled under an appropriate laminar flow hood. In this way, all of the stages for isolating and cultivating cells or for analyzing their genetic material can be conducted under sterile conditions.

According to particular features, the device of the present invention comprises a removable end-piece attached to the compartment in such a way as to be impermeable and removable; it is designed to restrict the relative movement of the mobile means and the compartment which enables said force to be applied to release said filter support.

Thanks to these provisions, the filter-holder is guaranteed to remain in position. Furthermore, the end-piece can protect it from splashes and contamination.

In this way, the filter is retained during filtration and then released so that it can be retrieved by removing the end-piece and by setting the movable means and the compartment respectively in motion in order to apply the force which releases the filter support.

According to a second aspect, the present invention relates to a process for isolating live cells on a filter or extracting their genetic material, characterized in that it comprises:

a step of attaching, at least temporarily, a filter to a lower opening of a compartment having, in addition, an air inlet, a step of inserting into said compartment a liquid carrying said cells, a step of attaching, in an impermeable manner, a needle, at least temporarily, to said compartment opening, the filter being positioned between the needle and the interior volume of the compartment, a step of perforation with said needle of a plug of a vacuum tube with negative pressure relative to ambient pressure and a step of aspiration, by means of negative pressure from the vacuum tube, of the liquid through said filter, said filter retaining said cells.

According to particular features, the process of the present invention, as briefly explained above includes, additionally:

a step of fastening a protective cylinder, at least temporarily, to the compartment, said protective cylinder then surrounding the needle and the vacuum tube being inserted into the protective cylinder during the perforation stage.

As the advantages, purposes and particular features of this process are similar to those of the device of the present invention, as briefly explained above, they are not repeated here.

BRIEF DESCRIPTION OF THE DRAWINGS

Other advantages, purposes and features of the present invention will emerge from the description which follows, provided for explanatory purposes and by no means exhaustive, with respect to the attached illustrations, in which:

FIG. 1, diagrammatically shown in perspective, represents the assembly of the parts of an initial embodiment of the device constituting the present invention, FIGS. 2A to 2D, diagrammatically shown in axial sections perpendicular to each other, represent the initial embodiment of the device before use, FIGS. 3A to 3O, diagrammatically shown in elevation or cross-section views, represent steps of implementation of the initial embodiment of the device constituting the present invention, FIG. 4, shown as a flow diagram, represents steps implemented in a particular initial embodiment of the process constituting the present invention, FIG. 5, diagrammatically shown in perspective, represents the assembly of the parts of a second particular embodiment of the device constituting the present invention, FIGS. 6A to 6D, diagrammatically shown in axial sections perpendicular to each other, represent the second embodiment of the device before use, FIGS. 7A to 7L, diagrammatically shown in elevation or cross-section views, represent steps implemented in the second embodiment of the device constituting the present invention, FIG. 8, shown in cross-section view, represents a filter support integrated into the second embodiment of the device constituting the present invention, FIG. 9, shown as a flow diagram, represents steps implemented in a second particular embodiment of the process constituting the present invention, FIG. 10 diagrammatically represents a particular embodiment of the device, before use, FIG. 11 diagrammatically represents the embodiment of the device illustrated in FIG. 10, after removal of a protective film and before insertion of a vacuum tube, FIG. 12 diagrammatically represents the embodiment of the device illustrated in FIGS. 10 and 11, after insertion of the vacuum tube, FIG. 13 diagrammatically represents the embodiment of the device illustrated in FIGS. 10 to 12, during removal of the vacuum tube and a protective cylinder and FIG. 14, shown as a flow diagram, represents steps implemented in a particular embodiment of the process constituting the present invention.

DETAILED DESCRIPTION OF THE EMBODIMENTS

Figure 2D:
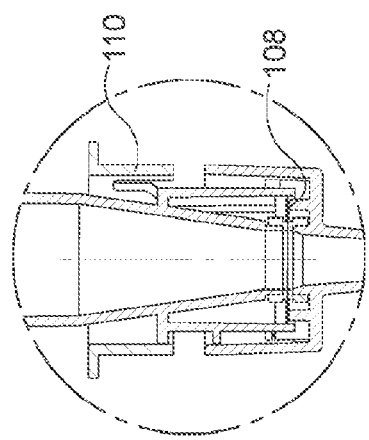

In the following description of the figures, a system is envisioned for the filtration of liquids, especially blood, which includes means for removing the filter support. However, the present invention is not restricted to these preferential embodiments but rather extends to any system comprising a compartment for receiving a liquid, a filter mounted, at least temporarily, onto an opening of this compartment and a needle mounted, at least temporarily and in such a way as to be leak-proof, onto this opening of the compartment so that as a plug of the pre-packaged vacuum tube is being pierced, the needle conveys aspirated liquid through the filter and the cells of interest are retained on this filter.

The needle has a very fine point designed to penetrate the plug of the vacuum tube (see FIGS. 3B to 3D) and a wider aperture designed to accommodate the lower end of the compartment or a filter support. The vacuum tube has considerable negative pressure and a volume larger than the volume of liquid to be filtered.

In preferential embodiments where the needle can be removed from the compartment, once the compartment is filled with the liquid containing the cells of interest, in order to collect the cells, the aperture of the needle is fitted over the opening of the compartment and the plug of the vacuum tube is then pierced with the fine point of the needle. Aided by negative pressure, filtration of the liquid is automatically performed, typically within 60 seconds.

In this way, filtration can be performed by holding the device by hand, which translates into significant savings of time and material, particularly because it is no longer necessary to provide a vacuum pump or an adaptor box for the compartment on the pump.

In addition, filtration can be performed in a sterile hood, so that the device can be slanted, or even placed horizontally.

The embodiments having a removable filter support and means for removing it from the compartment without touching it, will now be described.

FIG. 1 shows a reservoir, or compartment, 102, an end-piece 104, a seal 106, a filter with its support 108, a movable means 110, a seal 112 and a plug 114 with an air inlet (not shown).

The compartment 102 is cylindrically shaped. Its upper end can be sealed by the plug 114 in such a way that it is impermeable, except for the air inlet. The lower end of the compartment 102 has on its external surface, discontinuous rings with gaps which guide legs on the movable means 110, said rings guiding the body of the movable means 110.

This movable means 110 is generally cylindrical in shape and is supplied with two legs extending towards the end-piece 104 and narrowing together in this direction so that there is a separation between them measuring less than the diameter of the filter support 108. As will be subsequently illustrated, this particular shape, notably that of the legs 116 curved towards each other, enables the movable means 110, after it is removed from the end-piece 104, to apply pressure to the filter support 108 so that it is released from the compartment 102, along with its filter, while the movable means is being advanced towards the filter support 108.

The ends of the legs 116 of the movable means 110 and the lower end of the compartment 102 are designed to be inserted into a cell culture box or well. On the other hand, the diameter of the discontinuous ring at the end of the compartment 102 is designed so that the compartment can be supported on the edge of the cell culture box, or well.

Located at the lower opening of the compartment 102, so that it is impermeable, sterile and detachable, is an end-piece or adaptor, 104 which grips the exterior wall of the compartment 102 and has a lower narrow opening smaller in diameter than that of the compartment 102.

This lower narrow opening in the end-piece, or adaptor, 104 is sufficiently long to enable a leak-free mechanical fit of the aperture of a needle (see FIGS. 3B to 3D).

In a manner coordinated with the shape of the lower end of the compartment 102, which has lateral lugs 118, the end-piece 104 has rotation locking means for gripping said lugs in the manner known. In this way the end-piece 104 guarantees that the filter-holder is held in position during the filtration stages. In addition, the end-piece 104 protects the filter from splashes and contamination.

When attached, the lower end of the compartment 102 has an opening which discharges onto the filter held by the filter support 108, which is itself held in position, on the one hand, by the lower end of the compartment 102 and, on the other, by the end-piece 104.

The filter support 108 is, in the first embodiment, shaped as a ring-like disk. The filter is micro-perforated and is fused to the underside of the filter support 108, then inserted along with it into the lower end of the compartment 102.

The removable filter support 108 is preferably ring-shaped and made of surgical steel. Steel is actually not toxic to the cells collected on the filter. Furthermore, a filter support made of surgical steel is easier to remove than if it is made of plastic, and is firmer. The thickness of said ring is designed preferably to enable it to be scanned. This ring preferably carries an identifier. In this way, this identifier, and thus the cells collected, can be associated with a patient. Errors are thus avoided.

Alternatively, the filter support 108 is made of PVC and has a thickness less than or equal to 0.4 mm, and preferably less than 0.3 mm. Its external diameter is 12.6 mm, for example. The diameter of the filter to which the filter support 108 is attached is 5.9 mm, for example.

The compartment 102, the end-piece 104 and the movable means 110 are produced in polypropylene, for example. The seals 106 and 112 are made of silicone, for example.

Figure 2B:
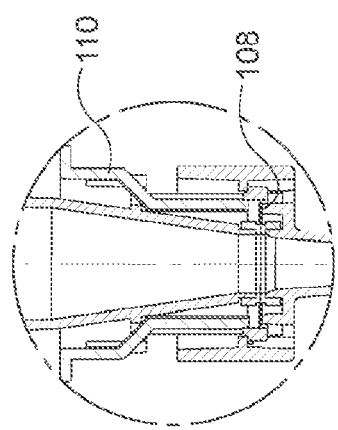
Figure 2C:
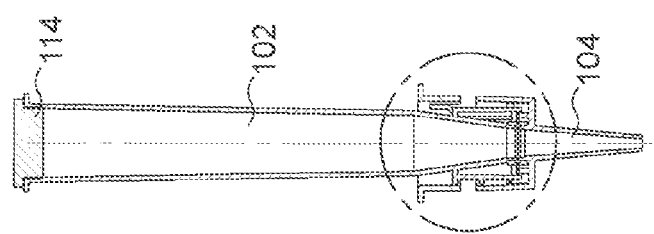
Figure 2A:
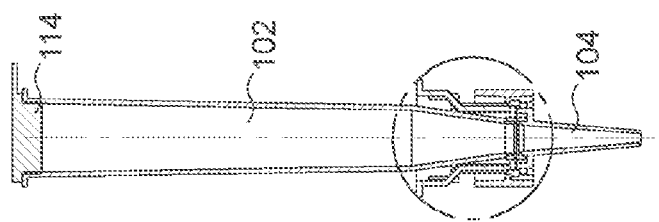

FIGS. 2A and 2C are views of perpendicular axial sections of the first embodiment of the device constituting the present invention, with the parts illustrated in FIG. 1 assembled. FIGS. 2B and 2D are enlarged detail views of the parts in FIGS. 2A and 2C, respectively. The elements described in relation to FIG. 1 are seen in FIGS. 2A and 2D.

FIG. 3A represents the device in elevation, in its storage configuration. FIG. 3B represents the insertion of the end-piece 104 into the aperture 181 of a needle 180 which has another very fine, beveled end 182 to make it easier to pierce a vacuum tube plug. The aperture 181 of the needle 180 is, preferentially, made of plastic. The end 182 of the needle 180 is, preferentially, metallic. The needle 180 can be positioned on the end-piece 104 either before or after liquid (not shown), for example blood, is introduced into the compartment 102, through its upper opening.

FIG. 3C illustrates the vacuum tube 185 plug 186 beginning to be pierced, once the needle 180 is impermeably joined to the end-piece 104.

FIG. 3D illustrates the plug 186 completely pierced through by the needle 180, connecting the interior of the negative pressure vacuum tube 185, through the filter 108, to the volume of the compartment 102 holding the liquid containing the cells of interest. The inner volume of the vacuum tube 185 is greater than the volume of the liquid to be filtered.

During aspiration, some particular cells in the liquid present in the compartment 102, which are larger in diameter, are retained by the filter 108 while the majority of the liquid, contents and, if necessary, the walls of the lysed cells and the cells smaller in dimension than the cells to be collected are aspirated into the vacuum tube 185, through the filter 108.

Next, as illustrated in FIGS. 3E and 3F, the end-piece 104 is removed after being rotated to release it from the lugs 118. Then, as illustrated in FIGS. 3G and 3H, the end of the compartment 102 is inserted into a cell culture box or well 130.

As explained above and illustrated in FIG. 3I, the end near to the legs 116 of the movable means 110 and the lower end of the compartment 102 are designed to be inserted into a cell culture box or well. In contrast, the discontinuous ring at the end of the compartment 102 has a diameter allowing it to be supported on the edge of the culture box or well 130.

To be more precise, as illustrated in FIGS. 3J and 3K, the movable means 110 can in this position still move parallel to the axis of the compartment 102.

As illustrated in FIGS. 3N and 3M, during this movement, the legs 116 of the mobile means when moved by the operator's fingers, apply vertical downward pressure on the filter support 108 and release it from the lower end of the compartment 102. The filter and its support 108 then fall into the cell culture box or well 130.

Lastly, as illustrated in FIG. 3O, the compartment 102 and the mobile means 110 are removed from the cell culture box or well 130.

Figure 4:
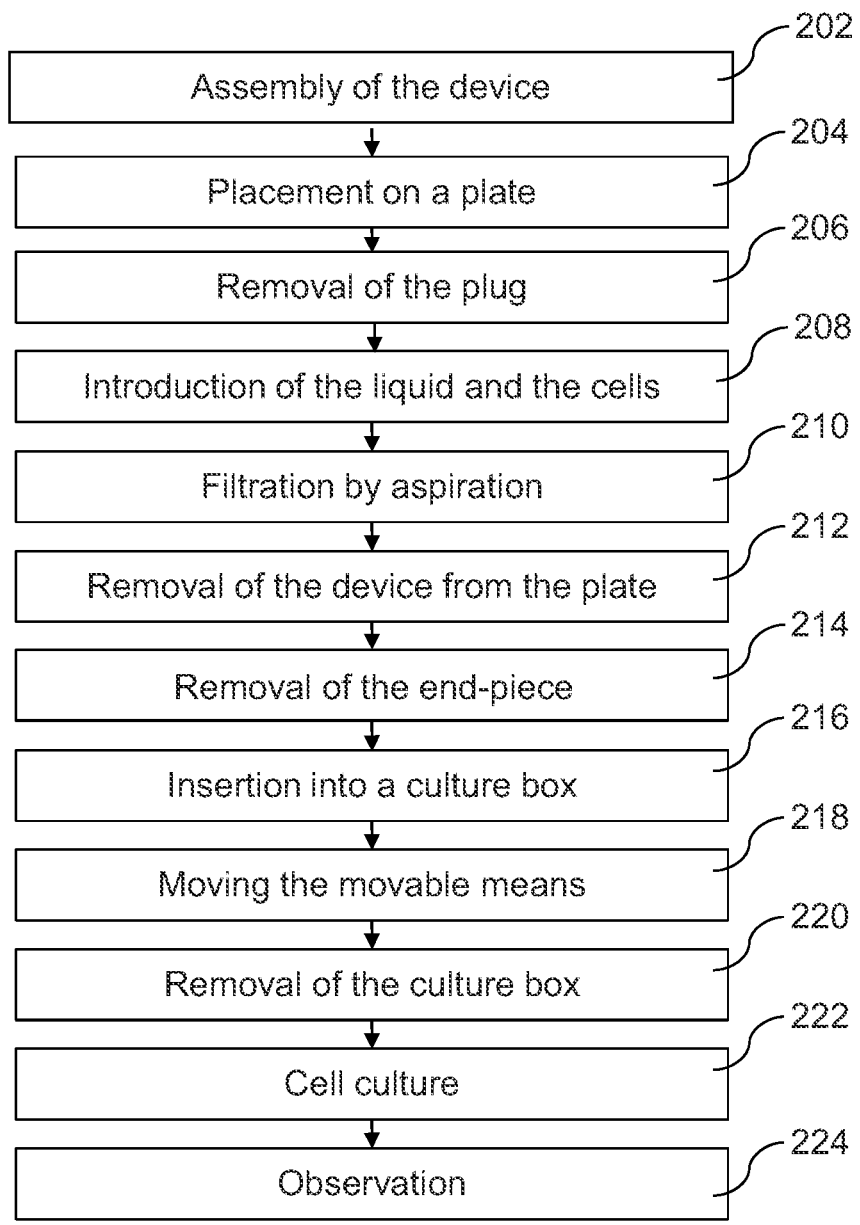

FIG. 4 summarizes the implementation of these stages.

During one stage 202, the parts of the device are assembled. During one stage 203, the plug 114 is removed. During one stage 204, the end-piece 104 is inserted into the aperture 181 of the needle 180. During one stage 205, a liquid containing cells to be isolated and possibly cultivated, blood for example, is introduced via the upper end of the compartment 102.

During one stage 206, the pointed end 182 of the needle 180 is positioned approximately in the centre of the plug 186 and pressure is applied to the compartment 102 to cause the needle to penetrate the plug 186 until the end of the needle reaches the interior volume, under negative or even vacuum pressure, of the vacuum tube 185.

During one stage 210, filtration is performed by aspiration of the cells smaller than the cells of interest, any lysed cells, and the majority of the liquid present in the compartment 102 into the vacuum tube 185, the cells of interest being retained on the filter 108.

During one stage 212, the vacuum tube 185 and the needle 180 are removed. During one stage 214, the end-piece 104 is removed. During one stage 216, the end of the compartment 102 is inserted into a cell culture box or well.

During one stage 218, the movable means and the compartment respectively are moved to exert force on the filter support 108 and release it so that it falls along with its filter into the cell culture box or well 130. During one stage 220, the compartment 102 and the movable means 110 are removed from the cell culture box or well 130.

During one stage 222, cell culture takes place, in the manner known, in the cell culture well 130. Note that the presence of the support 108 around the upper surface of the filter, the surface holding the cells isolated on the filter, prevents the cells from leaving the filter.

During the stage 222 where the culture of the live cells of interest takes place on the filter, the filter is covered with a thin layer of Matrigel, for example, (or brought into contact with a layer of Matrigel, a registered trademark, placed in advance on the bottom of the plate well and/or culture flask on which it is resting) containing factors designed to grow the cells of interest.

When observation of the cells, or their genetic material, is desired during a stage 224, the filter support 108 is retrieved using forceps; this is facilitated by the presence of lateral cylindrical holes, or recesses, in the upper surface of the filter support 108.

The filter support 108 can then be placed on a glass slide and the filter covered with a disc-shaped cover-glass of an appropriate diameter for the vacant upper surface of the filter. Analysis of the cells or extraction of their genetic material is carried out in the manner known.

FIG. 5 illustrates a reservoir, or compartment 302, an end-piece 304, a seal 306, a filter support 308, a movable means 310, a seal 312 and a plug 314.

The compartment 302 is generally cylindrical in shape. Its upper end can be impermeably sealed, with the exception of the air inlet (not shown), by the plug 314. The lower end of the compartment 302 has on its outer surface a cylinder 350 separated from the body of the compartment 302, except for mechanical connections in the form of lateral bands 352. This cylinder 350 has an outer diameter matching the inner diameter of the body of the movable means 310, so that it can be guided as it moves. The cylinder 350 is furnished with openings 354 designed to allow the legs 316 of the movable means 310 to be inserted and to slide longitudinally.

The movable means 310 has a generally cylindrical shape with two legs 316 extending towards the end-piece 304 and narrowing together in this direction so that there is a separation between them measuring less than the diameter of the filter support 308. As will be subsequently illustrated, this particular shape, notably that of the legs 316 curved towards each other, enables the movable means 310, after it is removed from the end-piece 304, to push the filter support 308 so that it is released from the compartment 302, as the movable means is advanced towards the filter support 308.

In a manner coordinated with the shape of the lower end of the compartment 302, which has lateral lugs 318, the end-piece 304 has rotation locking means for gripping said lugs in the manner known. In this way the end-piece 304 guarantees that the filter-holder is held in position during the filtration stages. In addition, the end-piece 304 protects the filter from splashes and contamination.

When fitted, the lower end of the compartment 302 has an opening which discharges onto the filter held by the filter support 308, which is itself held in position, on the one hand, by the lower end of the compartment 302 and, on the other, by the end-piece 304.

As illustrated in FIG. 8, the filter support 308 in the second embodiment is shaped to accommodate that of an Eppendorf tube.

In particular:

the interior upper part of the support 308 is shaped like the inner upper part of an Eppendorf tube, which allows the upper opening of said support to be closed with an Eppendorf tube plug and the exterior upper section of the support 308 conforms to the shape of the interior upper part of an Eppendorf tube, which allows the filter support 308 to be inserted into the top part of an Eppendorf tube.

In addition, the filter support 308 functions as a column to allow lysis of the cells retained on the filter and the centrifugal transfer of cellular lysate and genetic material from the filter support to the Eppendorf tube.

The filter support 308 is preferentially made of polycarbonate plastic. The compartment 302, the end-piece 304 and the movable means 310 are produced from polypropylene, for example. The seals 306 and 312 are made of silicone, for example.

Figure 6D:
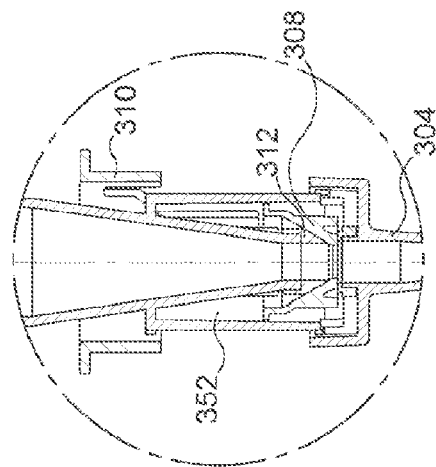
Figure 6C:
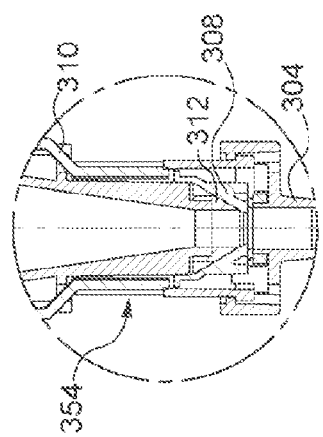
Figure 6B:
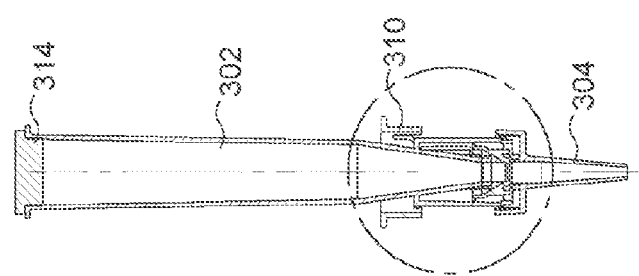
Figure 6A:
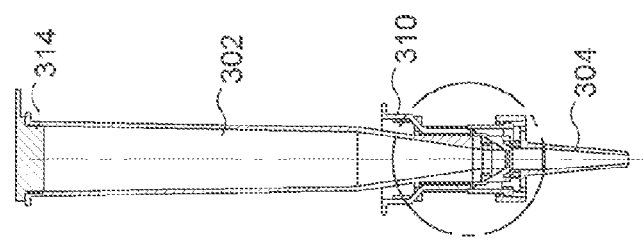

FIGS. 6A and 6C are mutually perpendicular axial sections of the second embodiment of the device constituting the present invention, when the parts illustrated in FIG. 5 have been assembled. FIGS. 6B and 6D are enlarged detail views of parts of FIGS. 6A and 6C, respectively. The elements described with respect to FIG. 5 are seen in FIGS. 6A to 6D.

FIG. 7A represents the device in elevation in its storage configuration. FIGS. 7B to 7D are identical to FIGS. 3B to 3D, except that the end-piece is referenced 304.

As illustrated in FIGS. 7E and 7F, the end-piece 304 is removed after it is rotated to release the lugs 318. Next, as illustrated in FIGS. 7G, 7H and 7I, the end of the compartment 302 is inserted into an Eppendorf tube support 328 supplied with an Eppendorf tube 330.

As illustrated in FIGS. 7J and 7K, the movable means 310 is then lowered parallel to the axis of the compartment 302. As it moves, the legs 316 of the movable means 310 when moved by an operator's fingers exert downward pressure on the filter support 308 and release it from the lower end of the compartment 302. The filter support 308 is then lowered into the Eppendorf tube 330.

Lastly, as illustrated in FIG. 7L, the compartment 302 and the movable means 310 are removed.

Figure 9:
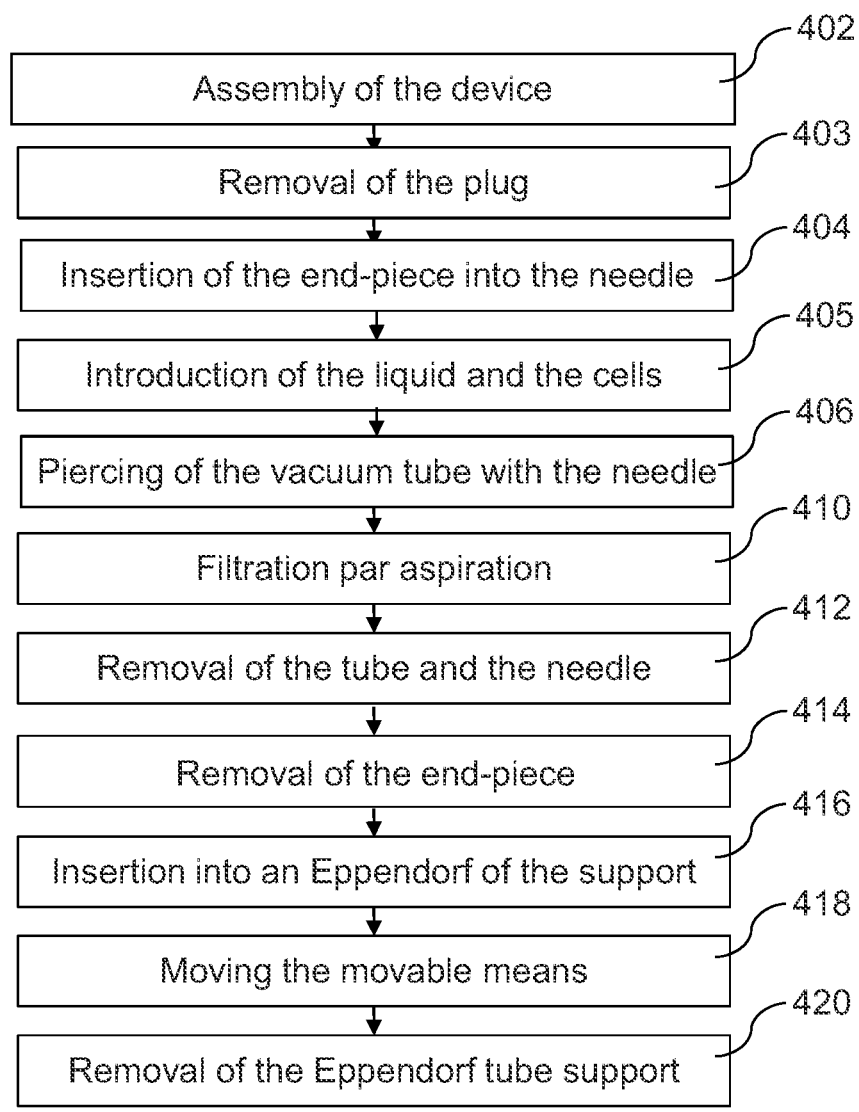

FIG. 9 summarizes the implementation of these stages.

During one stage 402, the parts of the device are assembled. During one stage 403, the plug is removed. During one stage 404, the plug 304 is inserted into the aperture 181 of the needle 180. During one stage 405, a liquid, containing cells to be filtered and possibly cultivated, blood for example, is introduced via the upper end of the compartment 302.

During one stage 406, the pointed end 182 of the needle 180 is positioned approximately in the centre of the plug 186 and force is applied to the compartment 302 to cause the needle to penetrate the plug 186 until the end of the needle reaches the interior volume, under negative or even vacuum pressure, of the vacuum tube 185.

During one stage 410, filtration is performed by aspiration of the cells smaller than the cells of interest and any lysed cells, and the majority of the liquid present in the compartment 302 into the vacuum tube 185.

During one stage 412, the vacuum tube 185 and the needle 180 are removed. During one stage 414, the end-piece 304 is removed. During one stage 416, the end of the compartment 302 is inserted into an Eppendorf tube support.

During one stage 418, the movable means and the compartment respectively are moved so that pressure is applied to the filter support to release it so that it falls into the Eppendorf tube. Lastly, during one stage 420, the compartment 302 and the movable means 310 are removed and the plug of the Eppendorf tube replaced.

The Eppendorf tube is then put to use in the manner known, for example with stages of lysis, centrifugation and collection of genetic material with or without pre-amplification of the entire genome.

During stages 422 and 424, an analysis is conducted on the genetic material collected at the bottom of the Eppendorf tube after centrifugation, particularly DNA and RNA from the desired cells. Amplified DNA is used as a matrix to detect variations in sensitivity or resistance to target treatments. Additionally, or alternatively, cDNA ("c" signifying complementary) derived from RNA by RT conversion, and amplified, is used as a matrix to detect gene expression levels for sensitivity or resistance to target treatments. This genetic material, when obtained from trophopblasts filtered from blood taken from expectant mothers, can be used to enable potential genetic abnormalities to be identified.

Using pairs of forward and reverse primers and pairs of probes during a quantitative real-time PCR ("polymerase chain reaction"), a defined volume of amplified genetic material, particularly DNA, is sampled to detect the variations in sensitivity or resistance to target treatments.

The principle of the research into variations in sensitivity and resistance to the target treatments implemented in the embodiment represented is as follows. Allelic discrimination or "SNP genotyping assay" (SNP being the acronym for single nucleotide polymorphism) enables information to be gathered about the presence or absence of an occasional variation in the gene. The first stage, 422, of allelic discrimination is a real-time quantitative PCR reaction conducted with two primers to amplify the sequence of interest, and two probes, for example TaqMan (registered trademark). One of the probes recognizes the mutated sequence and the other recognizes the normal sequence. The two probes are associated with different fluorochromes, for example, "VIC" fluorochromes for the probe hybridizing to the normal sequence and "FAM" fluorochromes for the probe hybridizing to the mutated sequence. The second stage, 424, uses an allelic discrimination program which measures the initial fluorescence and the final fluorescence produced by the FAM and/or VIC fluorochromes. This program allows the various sequences present in each sample to be distinguished:

an increase in VIC fluorescence alone indicates a homozygous profile for the normal sequence, an increase in FAM fluorescence alone indicates a homozygous profile for the mutated sequence, an increase in both VIC and FAM fluorescence alone indicates a heterozygous profile.

The probes are paired between the two primers and reveal the presence or absence of a mutation on the basis of the color of their associated fluorescence.

In other embodiments, a defined volume of genetic material, RNA in particular, converted into cDNA by RT (acronym for "reverse transcription") and amplified, is sampled in order to detect the gene expression level of sensitivity and resistance to target treatments using pairs of forward and reverse primers and a probe during a quantitative real-time PCR (acronym for "polymerase chain reaction") with 50 cycles, for example.

In each of the embodiments described above, the filter is produced preferably from polycarbonate plastic, and given a hydrophilic surface treatment. The use of such a filter increases the retention of the particular cells and reduces the adhesion of other cells or their contents, when they have specifically undergone lysis.

The filter has a pore diameter preferably centered on a value that is lower, by 1 μm for example, than the corresponding value used for the same cells that are fixed, i.e. made rigid.

For example, if the diameter of the pores for the fixed cells would have been centered on 7.5 μm, it is centered on a lower value, 6.5 μm for example. Due to the dispersion of the diameters, virtually no pore has a diameter above 7 μm.

For an application of the invention to blood cells, the filter has pores with a density between 50,000 and 200,000 pores/cm$^2$ and preferably approximately 100,000 pores/cm$^2$.

On account of the use of a polycarbonate plastic filter, the negative pressure required is much lower than in prior art systems, as much as four times lower, which prevents deterioration of the cells targeted for collection on the filter.

Where alternative variants exist, the filter support 108 or 308 is mechanically attached to the movable means until force is applied to release the filter support from the movable means by moving the compartment towards the culture well or the Eppendorf tube. A reversal of the roles of the lower end of the compartment 102 or 302 and the movable means 110 or 310 so that the latter holds the filter support in or in front of a glass slide a culture well or an Eppendorf tube and the former releases it when pressure is applied to the upper end of the compartment, is a adaptation easily within the ability of a person skilled in the art to perform, from the foregoing description of the embodiments.

FIGS. 10 to 14 relate to particular embodiments of the invention and the process constituting the present one, which use a protective guiding cylinder for the vacuum tube.

Although these particular embodiments supplement one or other of the embodiments described above, it has been decided to adapt them to the embodiment illustrated in FIGS. 1 to 4, in order to produce FIGS. 10 to 14.

FIGS. 10 to 13 show the compartment 102, the movable means 110 and a protective cylinder 502 attached to the compartment 102 by a two-part connection means, 504 and 520.

The protective cylinder includes the connection means part 504, a frosted part 506, a transparent part 508 and, on an opening facing the compartment 102, a film 510.

Part 520 is formed inside the end of the compartment 102. FIG. 13 shows a particular embodiment of part 520 comprising 4 prongs laterally positioned on a cylindrical part in co-axial relation to the compartment 102. In this embodiment, part 504 is comprised of four grooves with profiles corresponding to those of the prongs. These grooves 524 extend in a elliptical fashion, from an opening designed to accommodate a prong 522 towards the interior of the protective cylinder 502 so that by rotating the protective cylinder 502 as indicated by an arrow in FIG. 13 causes each prong 522 to advance into the corresponding groove 524 and the protective cylinder 502 to be tightened onto the compartment 102.

The protective cylinder 502 is attached to the end-piece carrying the needle 180 as follows. The needle 180 is embedded in the lower part of part 524, which is the part facing the compartment 502. Part 524 is force-mounted onto part 506 by means of 4 spokes. The spokes are located on part 504 and are inserted into four grooves located on part 506.

Part 506 serves to conceal the needle 180. The transparent part 508 enables the user to verify the status and completion of filtration.

Figure 10:
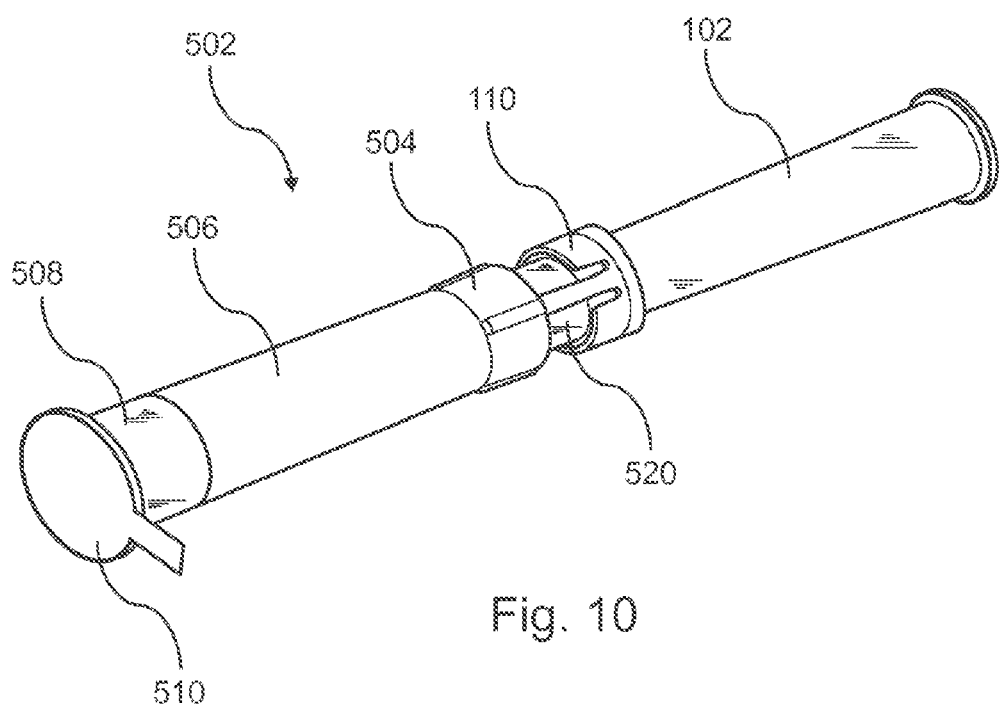

The film 510, which covers and seals the entire lower opening of the cylinder 502 is furnished with a lateral part extending a short distance from the cylinder 502 (illustrated in FIG. 10). This lateral part allows the film 510 to be easily removed.

The film 510 protects the user from access to the needle 180. The film 510 also protects the needle 180 from the risk of clogging and/or contamination.

The cylinder 502 is discreetly colored, for example blue, green or yellow, depending on the purposes for which the filtration device is used (cytological, molecular biology and culture studies, respectively).

Note in FIG. 11 that after the liquid to be filtered is inserted into the compartment 102 and the film 510 is removed, the vacuum tube 185 fitted with its plug 186 is inserted into the protective guiding cylinder 502. Force is then applied to the vacuum tube 185 so that the needle 180 pierces the plug 186, as explained above.

In the assemblage thus produced, shown in FIG. 12, the negative pressure initially present in the vacuum tube 185 brings about filtration of the liquid present in the compartment 102.

Note in FIG. 11 that after the liquid to be filtered is introduced into the compartment 102 and the film removed 510, the vacuum tube 185 fitted with its plug 186 is inserted into the protective guiding cylinder. A push is then applied to the vacuum tube 185 so that the needle 180 pierces the plug 186, as earlier described.

In the assemblage thus produced, illustrated in FIG. 12, the negative pressure initially present in the vacuum tube 185 causes filtration of the liquid present in the compartment 102.

When filtration is completed, as illustrated in FIG. 13, the protective cylinder 502 and the needle 180 it houses are jointly removed.

Figure 14:
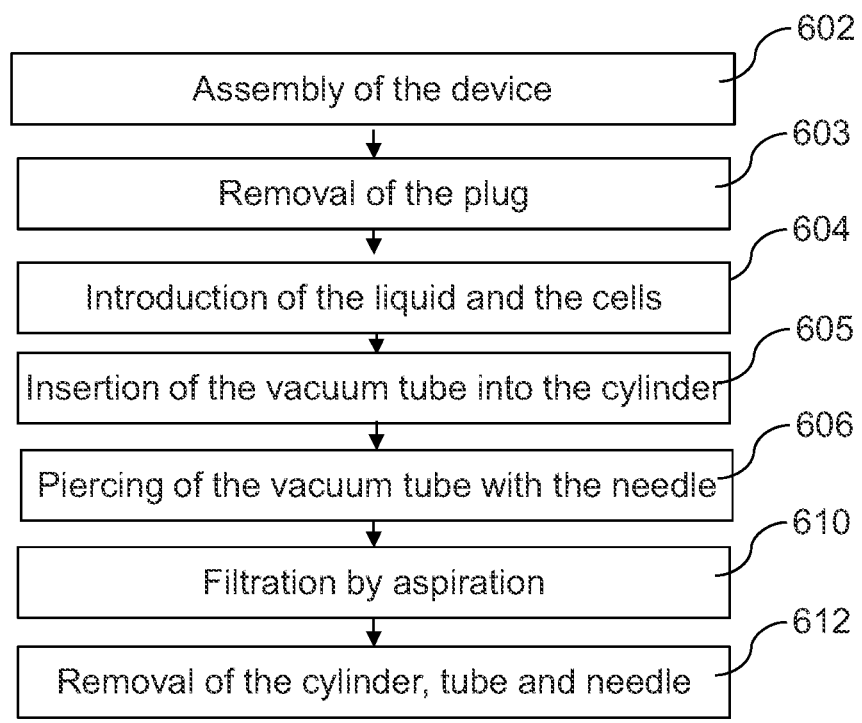

FIG. 14 summarizes the implementation of these stages.

During one stage 602, the parts of the device are assembled. During one stage 603, the plug 114 is removed. During one stage 604, a liquid, blood for example, containing cells to be isolated and possibly cultivated, is introduced via the upper end of the compartment 102.

During one stage 605, the vacuum tube 185 is inserted into the protective cylinder 502, which has the effect of positioning the pointed end 182 of the needle 180 approximately in the centre of the plug 186, and opposing force is applied to cause the needle 180 to penetrate the plug 186 until the end of the needle reaches the interior volume, under negative or even vacuum pressure, of the vacuum tube 185, during one stage 606.

During one stage 610, filtration is performed by aspiration of the cells smaller than the cells of interest and any lysed cells, and the majority of the liquid present in the compartment 102, into the vacuum tube 185, the cells of interest being retained on the filter 108.

During one stage 612, the protective cylinder 502, vacuum tube 185 and needle 180 are removed.

The following stages have already been explained with regard to the other embodiments and depend on these embodiments. They are therefore not described here again.

It will be understood from the preceding that while the protective cylinder is attached to the compartment, the user is protected against being accidentally pricked by the needle. Additionally, the positioning of the vacuum tube is facilitated through the guidance provided by the protective cylinder. The vacuum tube is also kept firmly in position during aspiration, which prevents it being removed or displaced thus allowing air to enter the vacuum tube by passing next to the needle in the vacuum tube plug. The risk of sample contamination by the user is minimized, as the user cannot inadvertently touch the needle.

Preferably, as illustrated in FIGS. 10 to 13, the device constituting the present invention comprises, at least provisionally, said protective cylinder. In other embodiments, assembly is carried out immediately before use.

Preferably, as illustrated in FIGS. 10 to 13, the connection means is provisional and enables the protective cylinder to be jointly removed with the vacuum tube. Where alternative variants exist, these two parts are removed in two successive steps.

In embodiments, the device constituting the present invention is presented in the form of a kit comprising, in an outer bag, two inner bags:

the first of which comprises the assembled device, as illustrated in FIGS. 2A, 6A and 10, and the second of which comprises the needle, the vacuum tube, the culture well and a circular slide and/or an Eppendorf tube or other useful accessory for using the device.

Use of the present invention makes it possible to avoid high-risk sampling of cells, for example amniotic fluid cells, while enabling cell cultures to be performed, for example for amniocentesis. Furthermore, due to the fact of the filter support 108 being shaped like a reservoir, immunocytochemical and fluorescent in situ hybridization ("FISH") reactions can be produced directly in this support.

The invention claimed is:

1. A device for isolating fixed or live cells on a filter or extracting genetic material from live cells, comprising:
    a compartment with an interior volume for receiving liquid carrying said cells, a lower opening and an air inlet;
    a movable means configured to be set in motion respectively with said compartment, said movable means having legs;
    a filter and filter support held by at least one of said compartment opening or said movable means, designed to retain said cells when liquid is passed through the filter;
    a needle forming a single impermeable unit, at least temporarily, with said compartment opening, the filter being positioned between the needle and the interior volume of the compartment, said needle being designed to pierce a plug of a vacuum tube with negative pressure relative to ambient pressure in order to aspirate the liquid through said filter;
    a connection means between the compartment and a protective cylinder surrounding the needle, said connection means being configured to surround, at least in part, the vacuum tube during aspiration of the liquid through the filter;
    wherein said movable means and the compartment are configured to be set in motion respectively in order to apply a force on the filter and release the filter after aspiration of the liquid through the filter; and
    wherein the legs of the movable means are configured, when moved by an operator's fingers, to exert downward pressure on the filter support and release the filter support from a lower end of the compartment.

2. The device according to claim 1, further comprising, at least provisionally, the protective cylinder.

3. The device according to claim 2, wherein the connection means is provisional and enables joint removal of the protective cylinder together with the vacuum tube.

4. The device according to claim 1, wherein the connection means is provisional and enables joint removal of the protective cylinder together with the vacuum tube.

5. The device according to claim 4, wherein the protective cylinder comprises a movable film sealing an opening of the protective cylinder facing the connection means, said opening being adapted to receive the vacuum tube into the protective cylinder after removal of the movable film.

6. The device according to claim 3, wherein the protective cylinder comprises a movable film sealing an opening of the protective cylinder facing the connection means, said opening being adapted to receive the vacuum tube into the protective cylinder after removal of the movable film.

7. The device according to claim 2, wherein the protective cylinder comprises a movable film sealing an opening of the protective cylinder facing the connection means, said opening being adapted to receive the vacuum tube into the protective cylinder after removal of the movable film.

8. The device according to claim 1, wherein the protective cylinder comprises a movable film sealing an opening of the protective cylinder facing the connection means, said opening being adapted to receive the vacuum tube into the protective cylinder after removal of the movable film.

9. The device according to claim 1, further comprising a surgical steel movable filter support adapted to be temporarily joined to a lower opening of the compartment.

10. The device according to claim 9, wherein the thickness of the filter support is adapted to enable the filter support to be scanned.

11. The device according to claim 10, wherein said filter support carries an identifier.

12. The device according to claim 9, wherein said filter support carries an identifier.

13. A process for isolating fixed or live cells on a filter or extracting the genetic material of live cells, comprising the steps of:
    attaching temporarily a filter and filter support to a lower opening of a compartment having, in addition, an air inlet or to a movable means configured to be set in motion respectively with the compartment, said movable means having legs;
    inserting into said compartment a liquid carrying said cells;
    attaching, at least temporarily, in an impermeable manner, a needle to said compartment opening, the filter being positioned between the needle and the interior volume of the compartment;
    fastening, at least temporarily, a protective cylinder to the compartment, said protective cylinder then surrounding the needle;
    perforation, with said needle, of a plug of a vacuum tube with negative pressure relative to ambient pressure, the vacuum tube being inserted into the protective cylinder during the perforation step;
    aspiration, by means of negative pressure from the vacuum tube, of the liquid through said filter, said filter retaining said cells;
    setting in motion respectively the moveable means and the compartment in order to apply a force on the filter and release the filter, wherein the legs of the movable means are configured, when moved by an operator's fingers, to exert downward pressure on the filter support and release the filter support from a lower end of the compartment.

14. The process according to claim 13, further comprising a step of jointly removing the protective cylinder together with the vacuum tube.

15. The process according to claim 14, wherein the protective cylinder comprises a movable film sealing an opening of the protective cylinder facing the connection means; and further comprising a step of removing the movable film before inserting the vacuum tube into the protective cylinder.

16. The process according to claim 13, wherein said protective cylinder comprising a movable film sealing an opening of the protective cylinder facing the connection means; and further comprising a step of removing the movable film before inserting the vacuum tube into the protective cylinder.

17. The process according to claims 13, further comprising between the steps of aspiration and setting in motion, the step of removing a removable end-piece, which is attached to the compartment to be impermeable and removable, wherein said end-piece is configured to restrict a relative movement of the movable means and the compartment.

18. The device according to claim 1, further comprising a removable end-piece attached to the compartment so as to be impermeable and removable, wherein said end-piece is configured to restrict a relative movement of the movable means and the compartment.

\* \* \* \* \*